US00PP10141P

United States Patent [19]

Auvil

[11] Patent Number: Plant 10,141

[45] Date of Patent: Dec. 9, 1997

[54] APPLE TREE: 'FUJI 216'

[75] Inventor: Grady Auvil, Oronda, Wash.

[73] Assignee: Auvil Fruit Company, Inc., Orondo, Wash.

[21] Appl. No.: 539,612

[22] Filed: Oct. 4, 1995

[51] Int. Cl.[6] ..... A01H 5/00

[52] U.S. Cl. ..... Plt./34.1

[58] Field of Search ..... Plt./34.1

[56] References Cited

U.S. PATENT DOCUMENTS

P.P. 7,997 10/1992 Yahagi ..... Plt./34.1

P.P. 8,032 11/1992 Cooper ..... Plt./34.1

P.P. 9,298 9/1995 Fukuda ..... Plt./34.1

P.P. 9,508 4/1996 Lynd ..... Plt./34.1

P.P. 9,645 9/1996 Van Leuven ..... Plt./34.1

*Primary Examiner*—James R. Feyrer

*Attorney, Agent, or Firm*—Christensen, O'Conne, Johnson & Kindness

[57] ABSTRACT

The Fuji 216 apple tree variety is characterized by the intense red coloration of its fruit, the high percentage of coloration of its fruit, and the early maturity of its fruit.

2 Drawing Sheets

FIELD OF THE INVENTION

This invention relates to a new and distinct variety of apple tree. The new variety is denominated Fuji 216.

DISCOVERY AND ASEXUAL REPRODUCTION OF THE TREE

The tree was discovered in September of 1993 in our cultivated apple orchard located at Vantage, Kittitas County, State of Washington. At that time we noticed a single limb mutation developed on a tree planted in 1991 on Mark rootstock. The tree is in a 21 acre block that was planted to a patented variety Tac 114 Fuji. At the time of discovery, we noticed that the single limb mutation on the 3-year-old Fuji tree had apples with significantly brighter color than the rest of the tree, as well as the other trees in the 21 acre block. The tree was flagged and we began monitoring the tree, and our quality control department began testing the apple for maturity.

We have carefully reviewed the limb and tree characteristics since that time and have found no differences in the leaves or growth of the sport limb as compared to the rest of the limbs.

In September of 1994, we removed several buds from the tree and asexually reproduced the new Fuji 216 variety into 2 trees in block 25. In March of 1994, we grafted 44 trees at our Vantage location and 1 tree at our Orondo location in Douglas County, State of Washington. In 1995 we monitored the apple on the original tree and one blossom from the bud in block 25 very carefully. In the spring of 1996, we planted 111,950 rootstock, and in the fall of 1996 budded the rootstock to Fuji 216. Also in 1996, we monitored development of apples from the parent Tac 114 Fuji tree, an adjacent tree, and the new Fuji 216 tree. We found that the characteristics of the new variety have remained the same in the progeny trees for three generations.

SUMMARY OF THE TREE

This new variety of apple tree is distinguishable from the parental Tac 114 Fuji variety by its fruit:

First, the apples of this new variety exhibit a more brilliant tone of red color.

Second, the apple color is a uniform blush, as compared to the narrow stripe on apples of the parent trees.

Third, the red coloration covered from 90% to 100% of the total apple surface by Sep. 7, 1995, when we harvested the apples. The intense color makes the apple from the new variety much more attractive in appearance than are the fruits of the parent apple varieties.

Fourth, the amount of fruit surface covered with red color significantly exceeds that of the parent strains of Fuji.

Fifth, the fruit of the new variety of Fuji apple are characterized by an advanced maturity. They developed a finished color and ripen from 5 to 21 days earlier than do the fruits of their predecessor Fuji strains. The early maturity of the fruits from the new Fuji 216 variety is of great economic importance, since it allows production of Fuji apples in areas where the growing season is too short for other Fuji strains to mature properly.

DETAILED BOTANICAL DESCRIPTION OF THE "Fuji 216" TREE

The observed tree, limb, and leaf characteristics of this new variety are essentially identical to the parental Tac 114 Fuji variety.

Tree: Low vigor, spreading, moderately branched, productive.

Trunk: Stocky, smooth, gray green to light brown.

Branches: Spreading, wide angles, medium thick, lenticels medium, dispersed, white to light brown, branches moderately from leaf axillary buds.

Internodes: Average internode distance equals 16 mm., the same as other Fuji trees in the block.

Leaves: *Primary.*—Broad, dark green, glossy on upper surface, moderately pubescent lower surface. Length: 80 to 100 mm. Width: 50 to 65 mm. Petiole: Short (25–35 mm.), thin (2–3.5 mm.), pubescent. Margins: Serrate. Tip: Moderately pointed. Bracts: Prominent, borne in pairs, opposite, narrow, pointed, born 5–6 mm. from abscission zone.

*Secondary.*—Oval, dark green upper surface, moderately pubescent lower surface. Length: 80 to 90 mm. Width: 40 to 50 mm. Margins: Medium serrate. Tip: Pointed. Petiole: Medium long (25–30 mm.), thin (1–1.5 mm.). Bracts: Obscure, borne in pairs, opposite, hairlike, borne 3–5 mm. from abscission zone.

Flowers: Mid-season (Apr. 10–20, Vantage, Wash.).

*Size.*—Medium.

*Color.*—White.

*Stamen.*—Single row, anthers are yellow, turning dark brown with pollen shed.

*Pistil.*—Stigmas: broad, flat at top, rounded at base. Styles: medium long, fused at base.

*Sepals.*—Medium size, pubescent.

Fruit: Maturity as described below. Eating ripe after 60 days cold storage. Good keeping qualities, holds flavor well.

*Size.*—Medium (85 mm.) to large (100 mm.).

*Form.*—Oval, slightly flattened at stem and calyx ends.

*Cavity.*—Round, narrow, deep: apex acuminate, breadth 25–35 mm., moderately pubescent.

*Stem.*—Medium short 10–25 mm. moderately thin 4.0 to 7.0 mm., moderately pubescent.

Figure 1:
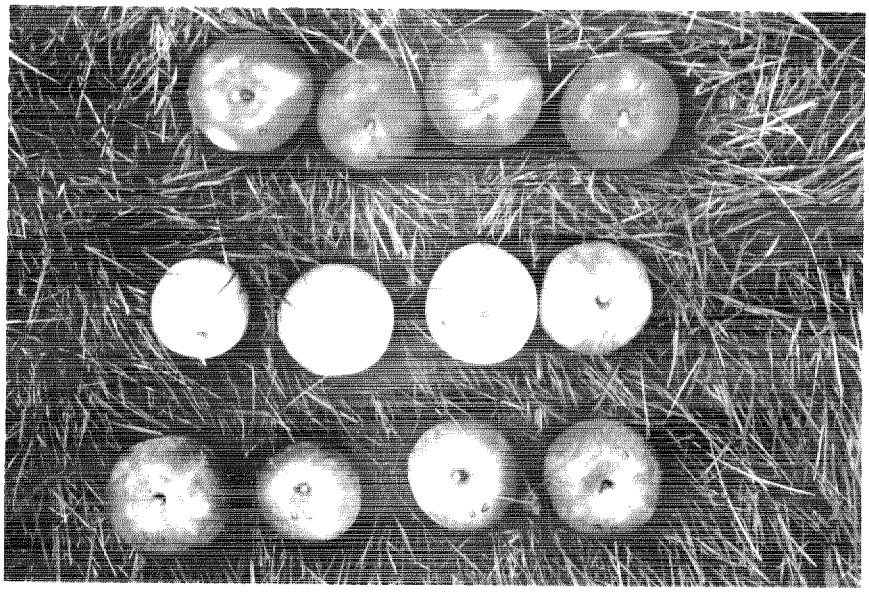
FIG. 1 shows 12 apples all picked in block 216 on Sep. 7, 1995. In the top row, numbers 1, 2, 3 and 4 are the new apples from the mutation limb. Numbers 1*a*, 2*a*, 3*a* and 4*a* (middle row) are representative apples from other limbs of the same tree. Numbers 1*b*, 2*b*, 3*b* and 4*b* (bottom row) are representative apples from an adjacent tree.
Figure 2:
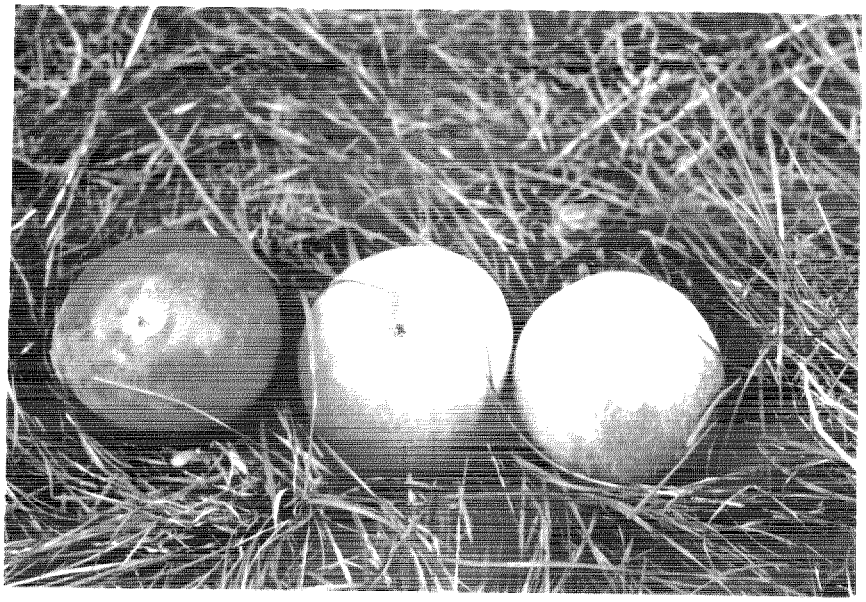
FIG. 2 shows three apples all picked in block 25 on Sep. 7, 1995. The red apple on the left is a second generation apple from the graft in block 25. The center apple is a representative apple from another ungrafted natural limb of the same tree. The right apple is a representative apple from another tree growing 15 feet away.

*Skin.*—Smooth, glossy, red (5R 4/12)[1] on red (5R 5/13) and yellow (Plate XVI, Color No. 21', Tone b)[2]. Red most prominent toward shoulder, thinning toward calyx, lenticels widely scattered, small. Red color covers 90 to 95% of the entire fruit surface (FIGS. 1 and 2) compared to 60 to 50% for standard Fuji in the same photo and 75 to 80% for a mature Tac 114.

[1]Nickerson Color Fan—Munsell Color Company: see *System of Color Notation*, Munsell, A.H. (Brigham Young University Library QC 494.3 M85X).

[2]*Ridgeway Color Standards & Nomenclature*: see *Color: Universal Language and Dictionary of Names*, Lowe, K. (Brigham Young University Library QC 494.3 K44X).

Figure 3A:
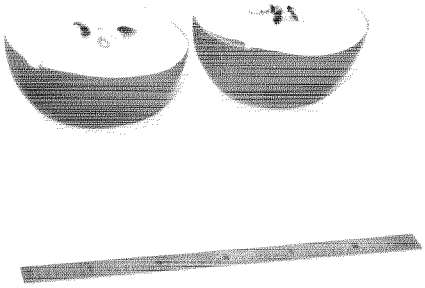
FIG. 3A shows two cut apples from the Fuji 216 variety compared to Fuji apples (FIG. 3B) from the same area on Sep. 15, 1995.
Figure 3B:
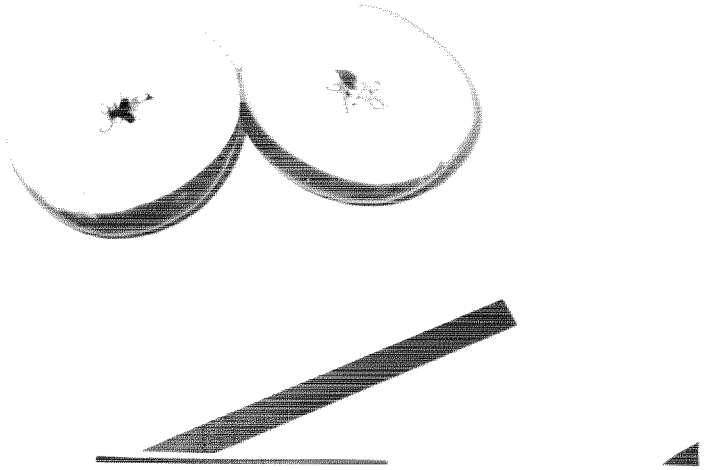

*Flesh.*—Creamy white (FIG. 3) turning very pale yellow with advanced maturity, juicy, sweet, smooth, tender, crisp, very fine.

*Aroma.*—Distinct, sprightly, moderately strong.

*Core.*—Sharply oval bundle area medium, bundles—prominent.

*Basin.*—Smooth, shallow, rounded.

*Calyx.*—Lobes absent sepals small, clasping, inconspicuous. Seeds: Medium size (6–7 mm. long; 4–5 mm. wide).

Date of fruit maturity: Sep. 14, 1994 and Sep. 7, 1995 in Central Washington State, 145 to 150 days after full bloom.

Pollination: Is satisfied by other diploid strains such as Golden Delicious, Winter Banana and commonly used strains of crab apples.

Use: Fresh; dessert.

Testing conducted in 1996 confirmed the differences between the parental TAC 114 Fuji variety and the new FUJI 216 variety. Such tests were conducted approximately weekly on apples from the parent tree, an adjacent TAC 114 tree, and a tree of the new Fuji 216 variety. Table 1 indicates the measurements of firmness (standard pressure test):

TABLE 1

| DATE | TAC 114 (Adjacent Tree) | TAC 114 (Parent Tree) | FUJI 216 |
|---|---|---|---|
| 8/7/96 | 23 | 19.5 | 18.5 |
| 8/13/96 | 23 | 17 | 15.5 |
| 8/20/96 | 22 | 15 | 14.5 |
| 8/27/96 | 20.5 | 14.5 | 16.5 |
| 9/3/96 | 20 | 14.5 | 15 |
| 9/10/96 | 17.8 | 14 | 14.8 |
| 9/17/96 | 17.7 | 14 | 12.3 |
| 9/24/96 | 16.5 | 12.7 | 12.3 |
| 10/1/96 | 16.5 | 12.5 | 12.5 |

Table 2 indicates measurements of S.S. (standard soluble solids measurement):

TABLE 2

| DATE | TAC 114 (Adjacent Tree) | TAC 114 (Parent Tree) | FUJI 216 |
|---|---|---|---|
| 8/7/96 | 9.4 | 8.8 | 9.6 |
| 8/13/96 | 8.8 | 10 | 10.2 |
| 8/20/96 | 10.6 | 10 | 10.8 |
| 8/27/96 | 10.8 | 11 | 11 |
| 9/3/96 | 11.4 | 12.2 | 12 |
| 9/10/96 | 11.7 | 12.7 | 12.7 |
| 9/17/96 | 12.5 | 12.7 | 13.5 |
| 9/24/96 | 13 | 13.7 | 14.6 |
| 10/1/96 | 13.7 | 13.67 | 14.0 |

Table 3 indicates starch measurements:

TABLE 3

| DATE | TAC 114 (Adjacent Tree) | TAC 114 (Parent Tree) | FUJI 216 |
|---|---|---|---|
| 8/7/96 | 1 | 1 | 1 |
| 8/13/96 | 1 | 1.5 | 1.5 |
| 8/20/96 | 1 | 2 | 2 |
| 8/27/96 | 1.5 | 2.5 | 2.5 |
| 9/3/96 | 1.25 | 4 | 3 |
| 9/10/96 | 1.67 | 3.7 | 3.7 |
| 9/17/96 | 1.67 | 2.8 | 3.3 |
| 9/24/96 | 2.83 | 5.3 | 4.7 |
| 10/1/96 | 2.83 | 5.0 | 5.3 |

Table 4 indicates diameter (inches):

TABLE 4

| DATE | TAC 114 (Adjacent Tree) | TAC 114 (Parent Tree) | FUJI 216 |
|---|---|---|---|
| 8/7/96 | 2.9 | 2.9 | 3.1 |
| 8/13/96 | 2.7 | 32 | 3.1 |
| 8/20/96 | 3.1 | 3.2 | 3.3 |
| 8/27/96 | 3.3 | 3.1 | 3.0 |
| 9/3/96 | 3.3 | 3.5 | 3.4 |
| 9/10/96 | 3.1 | 3.3 | 3.3 |
| 9/17/96 | 3.3 | 3.2 | 3.3 |
| 9/24/96 | 3.3 | 3.4 | 3.4 |
| 10/1/96 | 3.5 | 3.5 | 3.6 |

Table 5 indicates weight measurements (grams):

TABLE 5

| DATE | TAC 114 (Adjacent Tree) | TAC 114 (Parent Tree) | FUJI 216 |
|---|---|---|---|
| 8/7/96 | 201.5 | 193.2 | 214.3 |
| 8/13/96 | 146.0 | 245.4 | 236.4 |
| 8/20/96 | 236 | 239.5 | 272.0 |
| 8/27/96 | 300.6 | 220.5 | 199.9 |
| 9/3/96 | 222.4 | 295.8 | 286.3 |
| 9/10/96 | 240.1 | 263.4 | 277.0 |
| 9/17/96 | 287.4 | 247.3 | 254.2 |
| 9/24/96 | 281.5 | 267.7 | 292.4 |
| 10/1/96 | 339.1 | 293.2 | 277.0 |

Table 6 indicates water core measurements:

TABLE 6

| DATE | TAC 114 (Adjacent Tree) | TAC 114 (Parent Tree) | FUJI 216 |
|---|---|---|---|
| 8/7/96 | 0 | 0 | 0 |
| 8/13/96 | 0 | 0 | 0 |
| 8/20/96 | 0 | 0 | 0 |
| 8/27/96 | 0 | 0 | 0 |
| 9/3/96 | 0 | 0 | 0 |
| 9/10/96 | 0 | 0 | 0 |
| 9/17/96 | 0 | 0 | 0 |
| 9/24/96 | .67 | 2.67 | .33 |
| 10/1/96 | .67 | 1.67 | .67 |

Table 7 indicates color observations:

TABLE 7

| DATE | TAC 114 (Adjacent Tree) | TAC 114 (Parent Tree) | FUJI 216 |
|---|---|---|---|
| 8/7/96 | 50% red, very green background | 30% red, seeds turning brown | 65%, seeds turning brown |
| 8/13/96 | 75% red, seeds not turning brown | 30% red, seeds turning brown | 75%, all seeds brown |
| 8/20/96 | 65%–70% red | 25% red | 75%–80% red |
| 8/27/96 | 60% red | 30% red | 90% red |
| 9/3/96 | 50% red | 35% red | 95% red |
| 9/10/96 | 50%–60% red | 40%–50% red | 95%–100% red |
| 9/17/96 | 40% red | 40% red | 90%–100% red |
| 9/24/96 | 60% red | 40%–50% red | 95%–100% red |
| 10/1/96 | 90% red | 40%–50% red | 95%–100% red |

The above tables confirm the greater extent of coloration and earlier maturity of the new variety as compared to the parental Tac 114. As to the more brilliant tone of red color, the coloration is similar to that stated in U.S. Plant Pat. No. 8,032 on the Tac 114 variety. However, we have had extensive experience with the Tac 114 variety and have not been able to produce a color as bright or with as high a degree of red as stated in that patent. The new variety exhibits a more uniform blush and a more brilliant tone of red color then the parental Tac 114 tree, adjacent trees, and all other Tac 114 trees with which we have experience.

Based on our tests and observation, and the disclosures of U.S. Plant Pat. Nos. 8,032 and 7,997, a comparison summary of the newly discovered Fuji 2216 variety with other established varieties of Fuji apple tree is as follows:

(1) Standard Fuji has a significant degree of variation as to color pattern (some are striped and some blush). It apparently interacts with the growing conditions so that some years a given tree will produce both striped and/or blush fruit.

(2) The variety known as "Fuji Red Sport Type II" typically has more red color than standard Fuji (30–45% of the fruit surface is covered by red stripes).

(3) Fuji Tac 114 exhibits a higher degree of red color development, a more consistent striped color pattern, and matures 10–14 days earlier than does standard Fuji.

(4) The variety known as "Heisei Fuji" (U.S. Plant Pat. No. 7,997) appears to have some color characteristics similar to the new Fuji 216 variety, but is stated to mature in 150 to 160 days from full bloom, as compared to 175 to 185 days for its parent.

(5) Fuji 216 has substantially brighter and more extensive coloration than the above varieties and matures in 145 to 150 days, substantially earlier than even "Heisei Fuji."

Another new Fuji variety known as "Myra" is described in U.S. Plant Pat. No. 9,645. We have nine Myra trees growing in the general location of Tac 114 and our new Fuji 216 varieties at our orchard in Vantage, Wash. Fruit was first harvested from the Myra trees in 1996. The Myra trees were observed to bloom on Apr. 12, 1996, at approximately the same time as Tac 114 and Fuji 216. Some Fuji 216 apples were mature and ready for first harvest by Sep. 9, 1996, and harvesting continued until Sep. 23, 1996; Myra apples were mature and ready for first harvest on Oct. 1, 1996, with harvesting continued until Oct. 25, 1996; Tac 114 was mature and ready for first harvest on Oct. 3, 1996, with harvesting continuing until Nov. 2, 1996. In all cases minimum harvest maturity was as follows: 12 Brix soluble solids; white to yellow ground color; seeds black; 2.0 starch conversion. At maturity, Myra was observed to have a dull light pink red color over about 70% of the surface of the fruit, as compared to Fuji 216 which had a bright red color over a greater proportion of the surface of the fruit as set forth above. Since Fuji 216 matured substantially in advance of Myra with greater coloring, we preferred Fuji 216 to Myra and did not keep additional detailed statistical information for Myra.

I claim:

1. A new and distinct variety of Fuji apple tree substantially as herein shown and described.

* * * * *